(12) United States Patent
Kalchauer et al.

(10) Patent No.: US 6,252,102 B1
(45) Date of Patent: Jun. 26, 2001

(54) PROCESS FOR THE PREPARATION OF METHYLCHLOROSILANES

(75) Inventors: Wilfried Kalchauer, Burghausen; Herbert Straussberger, Mehring/Öd; Willibald Streckel, Mehring/Öd; Jochen Gross, Mehring/Öd, all of (DE)

(73) Assignee: Wacker-Chemie GmbH, München (DE)

( * ) Notice: Subject to any disclaimer, the term of this patent is extended or adjusted under 35 U.S.C. 154(b) by 0 days.

(21) Appl. No.: 09/671,751

(22) Filed: Sep. 27, 2000

(30) Foreign Application Priority Data

Oct. 27, 1999 (DE) .............................. 199 51 773

(51) Int. Cl.$^7$ ...................................... C07F 7/16
(52) U.S. Cl. ............................................. 556/472
(58) Field of Search ............................... 556/472

(56) References Cited

U.S. PATENT DOCUMENTS

| | | |
|---|---|---|
| 4,281,149 | 7/1981 | Shade . |
| 4,328,353 | 5/1982 | Shah . |
| 6,057,469 * | 5/2000 | Margaria et al. .................. 556/472 |
| 6,090,966 * | 7/2000 | Nakanishi et al. .................. 556/472 |
| 6,175,030 * | 1/2001 | Kalchauer et al. .................. 556/472 |

FOREIGN PATENT DOCUMENTS 0 784 057 A1  7/1997  (EP) .
0 900 802 A2  3/1999  (EP) .

OTHER PUBLICATIONS

"Silicon For The Chemical Industry II", Loen, Norway, Jun. 8–10, 1994, pp. 235–239.
"The Chemistry Of Organic Silicon Compounds", vol. 2, Part 2, Chapter 26, pp. 1581–1597, 1998.

* cited by examiner

Primary Examiner—Paul F. Shaver
(74) Attorney, Agent, or Firm—Brooks & Kushman P.C.

(57) ABSTRACT

In the process for the direct synthesis of methylchlorosilanes from chloromethane and silicon in the presence of a copper catalyst and promoter, the reaction mixture comprising chloromethane, methylchlorosilanes, and dust-like components comprising copper, promoter and silicon are removed continuously. The dust-like components are separated from the reaction mixture and cooled with liquid chloromethane.

16 Claims, No Drawings

PROCESS FOR THE PREPARATION OF METHYLCHLOROSILANES

TECHNICAL FIELD

The invention relates to a process for the Muller-Rochow direct synthesis of methylchlorosilanes in which isolated dust-like components of the reaction mixture are cooled with liquid chloromethane.

BACKGROUND ART

In the Muller-Rochow direct synthesis, chloromethane is reacted with silicon in the presence of a copper catalyst and suitable promoters to give methylchlorosilanes. In this process, as high a utilization of silicon as is possible in conjunction with safe and simultaneously flexible operation of the entire plant is required in addition to high productivity, as measured by the amount of silanes formed per unit time and reaction volume. High selectivity, based on the desired product dimethyldichlorosilane, is also desirable. Dimethyldichlorosilane is required, for example, for the preparation of linear polysiloxanes.

The direct synthesis can be carried out batchwise or continuously, the continuous procedure preferably being used in industrial production. The continuous direct synthesis is carried out in fluidized-bed reactors, in which chloromethane is used simultaneously as fluidizing medium and reactant. The silicon required is milled beforehand to a powder with a particle size of up to 700 $\mu$m, and is mixed with copper catalysts and promoters to give the catalyst material. This catalyst material is then introduced into the fluidized-bed reactor, and is reacted with the chloromethane at a temperature in the range of 260–350° C. Since the reaction is exothermic, the liberated heat of reaction must be removed via a cooling system.

Unconverted chloromethane, gaseous methylchlorosilanes, catalyst components and finely divided dusts leave the reactor. The coarser fraction of the entrained particles can be separated from the gas stream by means of one or more cyclones (main cyclones) and may be either recycled in whole or in part to the reactor, optionally via intermediate collecting containers, or alternatively may be removed from the system by means of dust collecting containers.

The very fine entrained particles must likewise be separated from the gas stream. This can be effected, for example, by gas filtration and/or by one or more downstream cyclones. High utilization of silicon can be ensured by this procedure. For example, such a system consisting of reactor, main cyclone with recycling and downstream cyclone with dust collecting container is shown in U.S. Pat. No. 4,281.149, FIG. 1. The crude silane is then separated from unconverted chloromethane and distilled. The refined, unconverted chloromethane can be fed back the reactor.

The collected dusts must be at least partially removed from the reaction system, since various secondary elements and slag components which are introduced with the silicon would otherwise accumulate in this product stream. When completely recycled to the reactor, selectivity will be greatly reduced by the catalytic effects of these impurities. Furthermore, finely divided, unreactive components which are introduced with the silicon, such as slags and iron suicides, must be removed from the system in order to achieve as high a productivity as possible. If the very fine dusts were to be completely recycled to the reactor, these dusts would be very rapidly discharged again and thus unnecessarily load the gas purification system: the selectivity and the reactivity would decrease owing to catalytic effects, and the production campaign would have to be shortened as a result.

These effects are described in B. Pachaly, H. Straussberger, and W. Streckel, "From Waste to Valuable Products: Work up of Silicon Metal Byproducts from the Direct Process", SILICON FOR THE CHEMICAL INDUSTRY II; Loen, Norway, Jun. 8–10, 1994; pages 235–239;. The dusts mainly comprise fine silicon particles, reacted silicon particles, slag particles, unreactive silicides, catalyst and promoter components and, on separation, have a temperature which corresponds approximately to the temperature of the contents of the reactor. Owing to the large specific surface area; to the presence of catalysts and promoters required for the direct synthesis; and to their free surface, i.e., one not covered with a protective $SiO_2$ layer, these dusts are very reactive. The dusts can, for example, further react with the chloromethane present and exothenrin in an uncontrolled manner. In "Recent advances in the direct process", THE CHEMISTRY OF ORGANIC SILICON COMPOUNDS; Volume 2, Part 2, Chapter 26, pages 1581–1597;, it is stated that the highly exothermic direct synthesis over silicon freshly milled in the absence of oxygen begins at 147° C. in the presence of the corresponding catalysts. The exothermic reaction of copper compounds with metallic silicon can also lead to uncontrolled exotherm from temperatures of about 150° C.

DISCLOSURE OF INVENTION

It was the object of the present invention to provide a process in which the above problems associated with the handling of the dusts generated in the direct synthesis of methylchlorosilanes are avoided.

BEST MODE FOR CARRYING OUT THE INVENTION

The invention relates to a process for the direct synthesis of methylchlorosilanes from chloromethane and silicon in the presence of a copper catalyst and promoter, in which a reaction mixture which comprises chloromethane, methylchlorosilanes and dust-like components comprising copper, promoter and silicon are removed continuously, separated from the gaseous reaction mixture, and cooled with liquid chloromethane.

The process is preferably carried out continuously. Usually, reactions with a substance which is gaseous at room temperature take place considerably more rapidly if this reactant is present in liquefied form. Thus, for example, liquid oxygen can react explosively with organic substances.

It has now been found that, as the result of the addition of a liquid chloromethane to the dust-like components of the reaction mixture, reactivity is considerably reduced by lowering the temperature. Since chloromethane is a component of the reaction mixture, its working-up, in particular the working-up of the methylchlorosilanes, is not made more difficult.

Chloromethane has a boiling point of –23° C. at ambient pressure, i.e. at 1013 mbar. By increasing the pressure, the boiling point can be correspondingly raised; for example, the boiling point at 2400 mbar is about 0° C. In a preferred embodiment, chloromethane with a pressure in the range from 2 to 7 bar and a temperature in the range from –6° C. to 31° C. is used, because this requires the least complexity in terms of apparatus.

If liquid chloromethane is now added to the hot dust-like components separated off, the chloromethane vaporizes and the dust is cooled without a vigorous exothermic reaction of the dust with the chloromethane occurring.

In a preferred embodiment, the dust-like components are separated off with the aid of one or more cyclones. The chloromethane is preferably added in such a way that the cyclone dust is cooled to a temperature in the range from 20° C. to 250° C. The temperature range from 75° C. to 145° C. is particularly preferred since this ensures that, on the one hand, the exothermic reactions of silicon with chloromethane and of silicon with copper compounds are substantially suppressed and, on the other hand, the methylchlorosilanes produced do not condense to a significant extent, which would complicate the transport of the cyclone dust.

By adding liquid chloromethane, effective cooling of the cyclone dust is ensured since, in contrast to cooling of the container wall or cooling by means of internal cooling coils, the cooling is effected directly in the interior of the container and no heat transferred through various materials is required.

In contrast, cooling of dusts which are not agitated or are only slightly agitated in dust collecting containers by cooling the corresponding container wall or by means of internal cooling coils is not very effective.

The mode of operation of a cyclone is such that the reaction mixture containing dust-like components is fed to the cyclone tangentially, a rotational movement being generated. Since the density of the dust particles is high compared with the gas density, the dust particles are spun outward by the centrifugal acceleration. They circle along the cylindrical wall of the cyclone to the apex of the cone, which apex is present in the lower part, and are discharged there. The gas from which dust has been removed leaves the cyclone through a central dip tube.

The chloromethane is preferably added at the apex of the cyclone cone or, if present, in the transition section between cyclone and dust collecting container or in the collecting container. As a result, the separation characteristic of the cyclone can be selectively changed as a function of the amount of gas. It is possible to ensure that very fine dust particles already separated off are discharged again via the central dip tube with the gas stream by means of the gaseous interfering stream in the lower region and/or below the cyclone. This is relevant in particular in the case of the main cyclones with dust recycling into the reactor, since this prevents very fine particles from being recycled into the reactor, which particles would then immediately be discharged again.

Preferably, a collecting container is arranged downstream of the apex of the cyclone cone. In particular, chloromethane is added in the collecting container. The reaction mixture is also preferably first passed through main cyclones and the gas partly freed from dust particles is passed into further cyclones. Chloromethane can be added at one or more points, and is preferably added via nozzles. The chloromethane, together with the chloromethane-containing crude silane, leaves the cyclone via the central cyclone dip tube.

The amount of chloromethane added depends, for example, on plant specifications, such as pressure resistance and heat resistance of the equipment; the desired cyclone separation characteristics; on the pressure and temperature of the liquid chloromethane; on the temperature and amount of cyclone dust separated; and on the desired cyclone dust temperature.

Depending on which advantage of the present invention is desired to be utilized, the chloromethane may be added continuously or only in discrete phases during the operation of the direct synthesis.

EXAMPLES

An industrial fluidized-bed reactor having continuous loading of catalyst material, main cyclone with dust recycling, downstream cyclone with dust removal via a dust collecting container, and an apparatus for spraying in liquid chloromethane into the separated dust fines is operated under comparable conditions (amount of dust, gas velocity, temperature, dust composition, . . . ) with an $Si/CuO/ZnCl_2/Sn$ catalyst material.

Comparative Example C1

No chloromethane is introduced into the system via the apparatus for spraying in liquid methyl chloride. The temperature in the dust collecting container increases in an uncontrolled manner to above 450° C., and the downstream plant equipment for dust transport, such as, for example, ball valves, can no longer be operated without problems, owing to the high temperature.

Example 1

Liquid chloromethane (2.4 bar) was sprayed into the dust collecting container via the apparatus for spraying in liquid chloromethane. The amount of chloromethane depends on the actual amount of dust and on the dust temperature and was between 10 and 250 l/h. By means of this procedure, the dust temperature can be kept constant in the range between 75 and 240° C. No problems occurred in the downstream dust transport units, and the cyclone dust obtained in the collecting containers contained a small amount of very fine fractions.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. In a process for the direct synthesis of methylchlorosilanes from chloromethane and silicon in the presence of a copper catalyst and promoter, in which a reaction product mixture which comprises chloromethane, methylchlorosilanes and, as dust-like components, copper, promoter and silicon are removed continuously and separated from the gaseous reaction mixture, the improvement comprising cooling the dust-like components with liquid chloromethane.

2. The process of claim 1, in which the dust-like components are separated with the aid of one or more cyclones.

3. The process of claim 1, wherein said liquid chloromethane is used at a pressure of from 2 to 7 bar and a temperature of from –6° C. to 31° C.

4. The process of claim 2, wherein said liquid chloromethane is used at a pressure of from 2 to 7 bar and a temperature of from –6° C. to 31° C.

5. The process of claim 1, wherein liquid chloromethane is added such that the dust-like components are cooled to a temperature in the range from 20° C. to 250° C.

6. The process of claim 2, wherein liquid chloromethane is added such that the dust-like components are cooled to a temperature in the range from 20° C. to 250° C.

7. The process of claim 3, wherein liquid chloromethane is added such that the dust-like components are cooled to a temperature in the range from 20° C. to 250° C.

8. The process of claim 4, wherein liquid chloromethane is added such that the dust-like components are cooled to a temperature in the range from 20° C. to 250° C.

9. The process of claim 2, wherein the liquid chloromethane is added at the apex of the cyclone cone.

10. The process of claim 2, wherein the liquid chloromethane is added in a transition section between the cyclone and a dust collecting container.

11. The process of claim 3, wherein the liquid chloromethane is added in a transition section between the cyclone and a dust collecting container.

12. The process of claim 5, wherein the liquid chloromethane is added in a transition section between the cyclone and a dust collecting container.

13. The process of claim 2, wherein the liquid chloromethane is added to a collecting container.

14. The process of claim 3, wherein the liquid chloromethane is added to a collecting container.

15. The process of claim 5, wherein the liquid chloromethane is added to a collecting container.

16. The process of claim 1, which is carried out continuously.

* * * * *